United States Patent [19]
Hayes

[11] Patent Number: 5,458,637
[45] Date of Patent: Oct. 17, 1995

[54] ORTHOPAEDIC BASE COMPONENT WITH MODULAR AUGMENTATION BLOCK

[75] Inventor: Kevin B. Hayes, Cordova, Tenn.

[73] Assignee: Zimmer, Inc., Warsaw, Ind.

[21] Appl. No.: 342,462

[22] Filed: Nov. 21, 1994

[51] Int. Cl.⁶ ..................................... A61F 2/38
[52] U.S. Cl. .................. 623/16; 623/18; 623/20
[58] Field of Search ................. 623/16, 18, 20, 623/22, 23

[56] References Cited

U.S. PATENT DOCUMENTS

| | | | |
|---|---|---|---|
| 4,731,086 | 3/1988 | Whiteside et al. | 623/20 |
| 4,769,039 | 9/1988 | Horber | 623/20 |
| 4,842,606 | 6/1989 | Kranz et al. | 623/23 |
| 4,911,721 | 3/1990 | Branemark et al. | 623/20 |
| 4,936,847 | 6/1990 | Manginelli | 623/23 |
| 4,944,757 | 7/1990 | Martinez et al. | 623/20 |
| 4,950,298 | 8/1990 | Gustilo et al. | 623/20 |
| 5,019,103 | 5/1991 | Van Zile et al. | 623/20 |
| 5,047,058 | 9/1991 | Roberts et al. | 623/20 |
| 5,071,438 | 12/1991 | Jones et al. | 623/18 X |
| 5,108,437 | 4/1992 | Kenna | 623/23 X |
| 5,108,452 | 4/1992 | Fallin | 623/23 |
| 5,152,797 | 10/1992 | Luckman et al. | 623/20 |
| 5,201,769 | 4/1993 | Schutzer | 623/23 |
| 5,344,461 | 9/1994 | Phlipot | 623/20 |
| 5,370,699 | 12/1994 | Hood et al. | 623/20 |

FOREIGN PATENT DOCUMENTS 2259253  3/1993  United Kingdom.

*Primary Examiner*—Mary Beth Jones
*Attorney, Agent, or Firm*—Margaret L. Geringer

[57] ABSTRACT

An orthopaedic base component and an augmentation block, such as a provisional tibial component 2, which includes an attachment mechanism that ensures that the augmentation block 30 can not inadvertently shift about or disconnect from the tray component 10. The attachment mechanism uses a button 40 and "key hole" shaped opening 20 to attach augmentation block 30 to tray component 10. The "key hole" opening is formed in the distal surface 14 of tray component 10. The "key hole" configuration is formed by an elongated slot 21 and a circular bore 23. Two oppositely facing protuberances 26 extend into the posterior end of each slot 21 from the peripheral side walls 22, which define the slot. Button 40 extends transversely from the proximal surface 34 of the augmentation block 30 and includes a substantially rectangular neck 42 and a flat circular head 44. Neck 42 has an indentation 43 formed on two opposed sides. Button 40 is securely held at the posterior end of slot 21 by protuberances 26, which are restrictively seated within the 43 in neck 42.

13 Claims, 2 Drawing Sheets

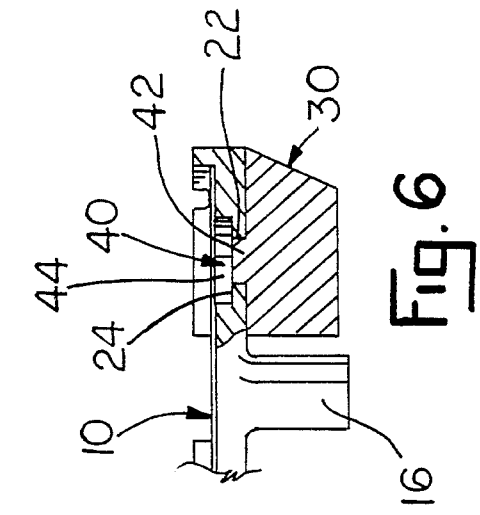
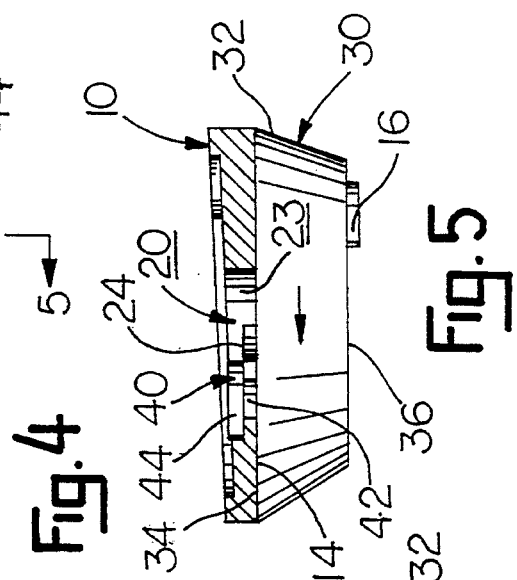
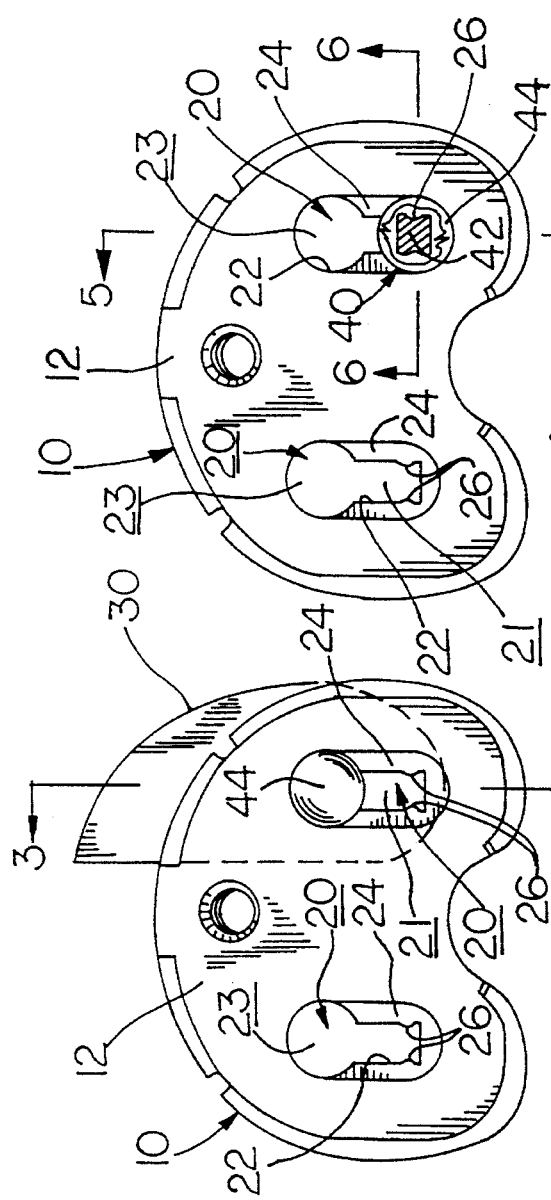
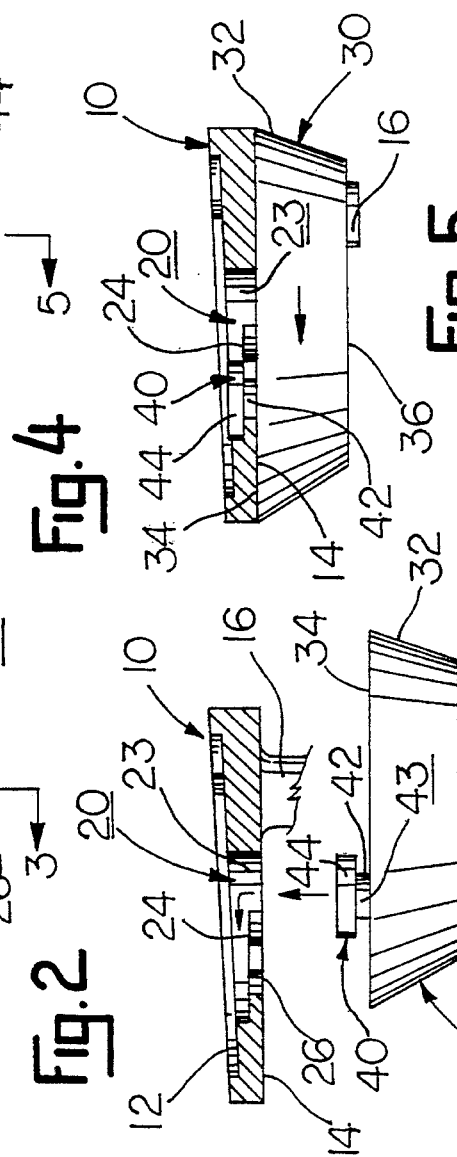

ORTHOPAEDIC BASE COMPONENT WITH MODULAR AUGMENTATION BLOCK

This invention relates generally to the field of orthopaedics, and in particular to an orthopaedic base component which has a modular attachment. The base component may suitably be either a base prosthetic implant component or a base implant provisional component.

BACKGROUND OF THE INVENTION

Implant prostheses and implant provisionals are well known in the field of orthopaedic joint replacement surgery. While this invention is particularly suitable for modular tibial implant provisionals having modular augment members, the features of this invention could also be utilized on other implant or provisional components which utilize modular augment members.

It is known in the art to utilize a provisional augment member with a base implant provisional member. Implant provisionals are used to test the surgeon's reshaping of the supporting bone and to provide a trial alignment for the implants. While the actual implant could be used to test the fit, it is more acceptable to use an implant provisional for such tests to prevent damage to the actual implant. U.S. Pat. No. 5,344,461 to Phlipot discloses a rotating dovetail attachment mechanism for connecting a modular provisional augment to a provisional tibial tray.

It is also known in the art to utilize augment members to provide an additional thickness of material onto the base implant. The following patents disclose various modular augment type members which are attached in various ways to a base implant component: U.S. Pat. Nos. 5,201,769; 5,152,797; 5,108,452; 5,047,058; 5,019,103; 4,950,298; 4,944,757; 4,936,847; 4,911,987; 4,842,606; 4,769,039; 4,731,086; and U.K. Patent Application GB 2 259 253A. U.S. Pat. No. 5,108,452 to Fallin discloses an augment in FIGS. 18–25 which includes a wedge locking member which fits into a socket to provide a wedge lock connection via mating inclined locking surfaces.

SUMMARY OF THE INVENTION

The base implant component or base implant provisional component and modular augmentation block of this invention includes an attachment mechanism for securely connecting the augmentation block to the base component. The attachment mechanism ensures that the augmentation block can not inadvertently shift about or disconnect from the base component. The attachment mechanism uses a locking button and "key hole" connection. A "key hole" shaped opening is formed in the distal surface of the base component (a provisional tibial tray component as illustrated in the figures). The "key hole" configuration is formed by an elongated slot and a circular bore. The peripheral side walls which define the slot are undercut to form an interior shoulder. Two oppositely facing protuberances extend into the posterior end of the slot. The button extends transversely from the proximal surface of the augmentation and includes a rectangular neck and a flat circular head. The neck has an indentation formed on two opposed sides. The button is inserted in the circular bore and slid posteriorly to the end of the slot to connect the augmentation block to the tray component. The button's neck is interposed between the slot's peripheral side walls and the button's head abuts the shoulder to prevent the button from being pulled directly from the slot. The button is secured at the posterior end of the slot and prevented from sliding forward along the slot by the protuberance, which extend into the indentations in the button's neck.

Accordingly, an advantage of this invention is to provide a base implant or provisional component and augmentation block which includes an attachment mechanism for connecting the augmentation block to the base component.

Another advantage of this invention is to provide a button and "key hole" attachment mechanism for a base implant or provisional component and augmentation block, which includes a locking mechanism to prevent the button from inadvertently disengaging from the "key hole" opening.

A further advantage of this invention is to provide an attachment mechanism to securely hold the augment in place, and yet which is simple to assemble at the time of surgery.

Other advantages will become apparent upon a reading of the following description.

BRIEF DESCRIPTION OF THE DRAWINGS

A preferred embodiment of the invention has been depicted for illustrative purposes only wherein:

FIG. 2 is a top view of the base provisional component showing the augmentation block spaced below the tibial tray;

FIG. 3 is a partial sectional view of the base provisional component taken along line 3—3 of FIG. 2;

FIG. 4 is a top view of the base provisional component showing the augmentation block attached to the tibial tray;

FIG. 5 is a partial sectional view of the base provisional component taken along line 5—5 of FIG. 4; and FIG. 6 is a partial sectional view of the base provisional component and augmentation block taken along line 6—6 of FIG. 4.

DESCRIPTION OF THE PREFERRED EMBODIMENT

Figure 1:
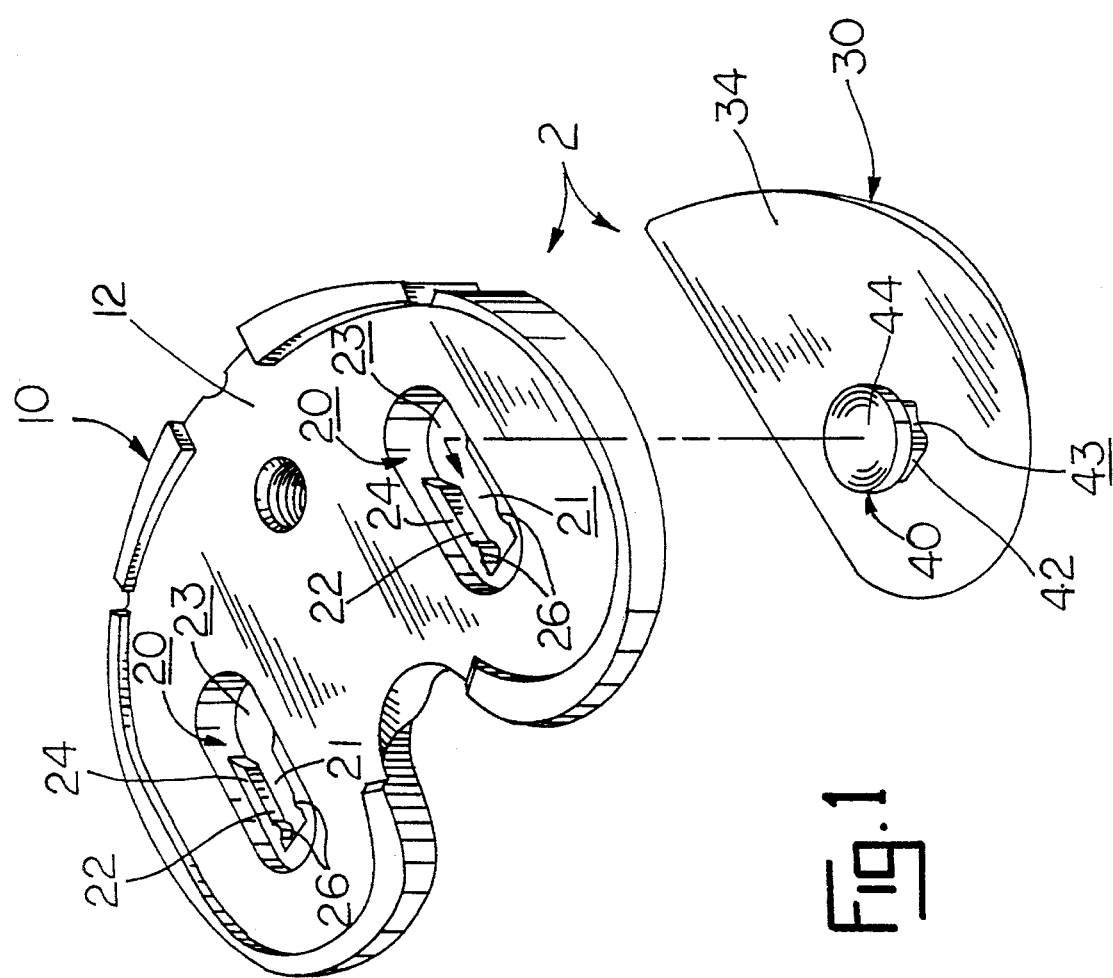
FIG. 1 is an exploded perspective view of a base provisional implant component, which includes a provisional tibial tray and a provisional augmentation block.

The preferred embodiment herein described is not intended to be exhaustive or to limit the invention to the precise form disclosed. It is chosen and described to explain the principles of the invention and its application and practical use to enable others skilled in the art to utilize its teachings.

The figures illustrate a provisional tibial implant component 2 for a knee joint prosthesis; although, the teaching of this invention can be incorporated into any implant or provisional implant component, which includes at least one attachable augmentation block. The locking attachment mechanism of this invention can be used with provisional components, as well as with actual implants. The terms: anterior, posterior, distal, and proximal used in this description of the preferred embodiment have specific relevance to implant prostheses and provisionals and are commonly used and understood in the art.

Provisional component 2 includes a base tray component 10 and a modular augmentation block 30. In practice, a set of augmentation blocks could be provided to the surgeon to provide a plurality of augment choices having different thicknesses and/or angular orientations. With the set of augmentation blocks, the surgeon may build the optimum implant provisional for the patient. The use of augmentation block sets is well known in the industry and is understood by ones skilled in the art. For illustrative purposes and ease of discussion, only one augmentation block 30 is shown and discussed herein.

Tray component 10 has a first bottom or distal surface 14 and a second upper or proximal surface 12. Proximal surface 12 is configured to accommodate a bearing insert (not shown) for sliding engagement with the femoral component of the knee (also not shown). A post or stem 16 (FIG. 6) extends from distal surface 14 and may be generally perpendicular to tray component 10, as shown, or at an acute angle (not shown). As is well known in the art, stem 16 is configured for insertion into a prepared intramedullary canal of the tibia. The anterior edge of the tray component may be arcuate.

A "key hole" shaped opening 20 is formed in the distal surface of tray component 10 on each side of the stem 16. Preferably, openings 20 are substantially parallel to each other, longitudinally situated in tray 10. The "key hole" shaped configuration of opening 20 is formed by an elongated posterior slot 21 and an enlarged circular anterior bore 23. As best shown in FIG. 1, the peripheral side wall 22 which defines slot 21 is undercut to form a shoulder 24. As shown in FIG. 1, two oppositely facing protuberances 26 extend into the posterior end of slot 21 from side walls 22. The opposite side walls 22 of slot 21 are substantially parallel to each other.

Modular augmentation blocks 30 (only one shown) may be suitably shaped to have an outer periphery 32 which is angled from its proximal surface 34 toward its distal surface 36, such that the edge of the proximal surface 34 of the outer periphery of augmentation block 30 is in alignment with the edge of the tray's distal surface 14. The outer periphery 32 follows the periphery of approximately one third of tray component 10 as illustrated in FIGS. 1 and 2, although it is well known in the art to provide such partial (e.g. one third or one half) augments, as well as full augments. Distal surface 36 of augmentation block 30 is substantially flat, although it is also well known in the art to provide various angles on the distal surface.

A button 40 extends transversely from the proximal surface 34 of block 30 and includes a substantially rectangular neck 42 and an enlarged flat circular head 44. The width of neck 42 is substantially equal to the width of slot 21 and has an indentation 43 formed on two opposed sides to mate with the two oppositely facing protruberances 26. Similarly, head 44 is substantially the width of slot 20.

FIGS. 2–5 illustrate in progression the method of attaching the augmentation block 30 to tray component 10. As shown in FIG. 3, button 40 is inserted into anterior bore 23. Once properly aligned, augmentation block 30 is slid to the posterior end of slot 21. As shown in FIG. 6, neck 42 is interposed between opposite side walls 22. Head 44 lies flat against shoulder 24 and mating proximal surface 34 of augmentation block 30 lies flat against first distal surface 14 of tray 10. The rectangular configuration of neck 42 helps ensure that augmentation block 30 slides linearly. As shown in FIG. 4, protuberances 26 are restrictively seated within indentation 43 in neck 42. Protuberances 26 provide a locking mechanism to prevent button 40 from sliding forward along slot 21. Manual force is applied in a longitudinal direction along slot 21 to assemble or disassemble the augmentation block 30.

It is noted that the "key hole" shaped opening could be formed on the modular augmentation block, and the button could be formed on the base or tray component, if desired. It is further noted that any suitable materials and manufacturing methods may be utilized for the base component and augment component, including any suitable plastic or metal material or any suitable combination thereof.

It is understood that the above description does not limit the invention to the details given, but may be modified within the scope of the following claims.

I claim:

1. An orthopaedic assembly comprising:

a base component having a first outer surface and an augmentation block having a mating surface configured to abut against said first outer surface of said base component, said base component having an elongated opening defined in said first outer surface, said augmentation block includes a button part protruding from said mating surface of said augmentation block and shaped to be shiftably inserted into said opening for connecting said augmentation block to said base component, said base component includes a first protuberance extending into said opening for engaging said button to secure said button at one end of said opening when said augmentation block is connected to said base component.

2. The orthopaedic assembly of claim 1 wherein said button includes a neck part having a first indentation, said protuberance engaging said neck within said indentation to secure said button at said one end of said opening when said augmentation block is connected to said base component.

3. The orthopaedic assembly of claim 2 wherein the base component includes a second protuberance extending into said opening and oppositely located from the first protuberance and the neck part includes a second indentation oppositely located from the first indentation, said first and second protuberances engaging said first and second indentations in said neck part when said block is connected to said base component.

4. The orthopaedic assembly of claim 2 wherein said opening is partially defined by a peripheral side wall, said side wall including a shoulder protruding around said one end of said opening, and wherein said first protuberance extends from said peripheral side wall into said opening, said button also including an enlarged head part on said neck part, said head part slidably abuts said shoulder when said button is slid to said one end of said opening while said neck part aligns with said peripheral side wall.

5. The orthopaedic assembly of claim 4 wherein said elongated opening is key hole shaped and includes a slot formed by said peripheral side wall and further includes an enlarged bore at an opposite end of the opening from the one end of the opening, said enlarged bore sized to receive the enlarged head part of the button upon assembly of the block to the base component.

6. The orthopaedic assembly of claim 1 wherein said base component is a provisional tibial tray component.

7. An orthopaedic assembly including a base component having a first outer surface, and an augmentation block having a mating surface configured to engage said first outer surface of said base component, the improvement comprising: an attachment means for connecting said block to said base wherein said base component has an elongated opening defined in its said first outer surface, said augmentation block includes a button part protruding from said mating surface of said augmentation block and shaped to be shiftably inserted into said opening to connect said augmentation block to said base component, said base component includes a protuberance extending into said opening for engaging said button to secure said button at one end of said opening when said augmentation block is connected to said base component.

8. The orthopaedic assembly of claim 7 wherein said button includes a neck part having an indentation, said protuberance is restrictively seated within said neck to secure said button at said one end of said opening.

9. The orthopaedic assembly of claim 7 wherein said opening is partially defined by a peripheral side wall, said side wall including a shoulder protruding around said one end of said opening, said button also including a head part, said head part shiftably abuts said shoulder when said button is slid to said one end of said opening.

10. The orthopaedic assembly of claim 7 wherein said elongated opening is key hole shaped.

11. An orthopaedic assembly comprising:

a base component having a first outer surface and an augmentation block having a mating surface configured to abut against said first outer surface of said base component, one of said first outer surface of said base component and said mating surface of said augmentation block having an elongated opening defined therein, and the other of said first outer surface and said mating surface including a button part extending therefrom, said button part shaped to be shiftably inserted into said opening for connecting the augmentation block to said base component, said opening including a first protuberance extending into said opening for engaging said button at one end of said opening when said augmentation block is connected to said base component.

12. The orthopaedic assembly of claim 11 wherein said button includes a neck part having a first indentation, said protuberance engaging said neck within said indentation to secure said button at said one end of said opening when said augmentation block is connected to said base component.

13. The orthopaedic assembly of claim 11 wherein said opening is partially defined by a peripheral side wall, said side wall including a shoulder protruding around said one end of said opening, said button also including a head part, said head part shiftably abuts said shoulder when said button is slid to said one end of said opening.

* * * * *